(12) United States Patent
Fujii et al.

(10) Patent No.: US 7,396,511 B2
(45) Date of Patent: Jul. 8, 2008

(54) DISPENSING DEVICE, DISPENSING METHOD AND METHOD OF DETECTING DEFECTIVE DISCHARGE OF SOLUTION CONTAINING BIOLOGICAL SAMPLE

(75) Inventors: Masahiro Fujii, Nagano (JP); Hiroshi Koeda, Nagano (JP); Fumio Takagi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 358 days.

(21) Appl. No.: 10/626,828

(22) Filed: Jul. 25, 2003

(65) Prior Publication Data
US 2004/0058438 A1 Mar. 25, 2004

(30) Foreign Application Priority Data
Jul. 26, 2002 (JP) ............. 2002-218650

(51) Int. Cl.
B41J 29/38 (2006.01)
B41J 2/045 (2006.01)
B01L 3/00 (2006.01)

(52) U.S. Cl. .............. 422/100; 347/10; 347/19; 347/68; 436/180

(58) Field of Classification Search ............ 347/10, 347/19, 68
See application file for complete search history.

(56) References Cited

U.S. PATENT DOCUMENTS

| | | | | |
|---|---|---|---|---|
| 4,484,199 A | * | 11/1984 | Watanabe | 347/19 |
| 4,631,554 A | * | 12/1986 | Terasawa | 347/30 |
| 4,877,745 A | * | 10/1989 | Hayes et al. | 436/166 |
| 5,563,634 A | * | 10/1996 | Fujii et al. | 347/9 |
| 5,668,579 A | * | 9/1997 | Fujii et al. | 347/10 |
| 6,174,038 B1 | | 1/2001 | Nakazawa et al. | |
| 6,257,694 B1 | | 7/2001 | Tokumaru et al. | |
| 6,329,209 B1 | * | 12/2001 | Wagner et al. | 436/518 |

(Continued)

FOREIGN PATENT DOCUMENTS

JP 58-181545 12/1983

(Continued)

OTHER PUBLICATIONS

English Translation of Notice of Reasons for Rejection in JP 202-218650 mailed Jan. 18, 2007, 3 pages.

*Primary Examiner*—Jill Warden
*Assistant Examiner*—Paul S Hyun
(74) *Attorney, Agent, or Firm*—Sterne, Kessler, Goldstein & Fox P.L.L.C.

(57) ABSTRACT

Proposed is dispensing technology capable of reliably spotting a biological sample on a solid phase. A head chip applies a voltage pulse between a diaphragm and separate electrodes based on a drive control signal output from a head driver IC, and discharges a solution containing protein filled in a pressurized chamber as a result of the elastic deformation of the diaphragm. A drive pulse generation circuit generates a drive voltage pulse and supplies this to the head chip in order to discharge a solution containing protein from the head chip. The drive current detection circuit detects a drive current flowing between the diaphragm and separate electrodes. Since the waveform of the detected drive current and the peak current value and so on differ in the case where the discharge status is normal and in the case where it is abnormal, a defective discharge can be discriminated by detecting such change.

12 Claims, 7 Drawing Sheets

U.S. PATENT DOCUMENTS

6,347,857 B1 *   2/2002   Purcell et al. .................. 347/19
6,640,621 B2 *  11/2003   Ward et al. .................. 73/118.2

FOREIGN PATENT DOCUMENTS

| JP | 04-007159 | 1/1992 |
| JP | 05-024194 | 2/1993 |
| JP | 08-187881 | 7/1996 |
| JP | 9-295411 | 11/1997 |
| JP | 11-187900 | 7/1999 |
| JP | 11-334102 | 12/1999 |
| JP | P2000-15790 A | 1/2000 |
| JP | 2002-052742 | 2/2002 |

* cited by examiner

FIG.1

100 PROTEIN DISPENSING DEVICE

FIG.2

10 MICRODISPENSER ARRAY

DISPENSING DEVICE, DISPENSING METHOD AND METHOD OF DETECTING DEFECTIVE DISCHARGE OF SOLUTION CONTAINING BIOLOGICAL SAMPLE

BACKGROUND OF THE INVENTION

1. Field of the Invention

The present invention generally relates to dispensing technology for spotting a biological sample such as protein or nucleic acid on a solid phase, and particularly to improved technology suitable in preparing a microchip.

2. Description of the Related Art

Pursuant to the advancement in biotechnology, human genome has been decoded, and genetic research is making a transition to the stage of structural analysis and functional analysis of protein. For instance, in the research of medicine or the like, research concerning proteomics; that is, how proteins relate to medical conditions as well as the development of chemicals capable of suppressing the working of such proteins, is becoming increasingly important. In this type of proteomics research, employed is a protein chip in which various proteins are spotted on a substrate. As a preparation method of such a chip, for example, as disclosed in Japanese Patent Laid-Open Publication No. H11-187900, known is a method of discharging a solution containing various proteins from an inkjet head and spotting this on a solid phase.

SUMMARY OF THE INVENTION

Nevertheless, generally speaking, a protein solution is highly viscous, and, since such viscosity varies depending on the type of protein, it is difficult to realize stable discharge characteristics upon performing spotting on a solid phase with an inkjet head. In particular, when the trajectory of the protein solution becomes unstable, cross contamination will occur, and it is therefore difficult to prepare a high quality protein chip. Further, with conventional methods, there are problems in that much time is required for preparing a protein chip formed of a large variety of proteins, the production efficiency is thereby inferior, proteins would become deactive with the lapse in time, and the reliability of the protein chip would deteriorate as a result thereof. Similar problems also arise upon preparing a DNA microarray.

Accordingly, an object of the present invention is to propose dispensing technology enabling the reliable spotting of a biological sample on a solid phase. Another object of the present invention is to realize a faster preparation of microchips.

In order to achieve the foregoing objects, the dispensing device according to the present invention comprises: a plurality of discharge means for discharging a solution containing a biological sample; discrimination means for discriminating the existence of a defective discharge of the solution in the discharge means; and control means for selecting the discharge means in which the discharge status is not defective as a result of discriminating the defective discharge with the discrimination means, and performing discharge control of the solution containing the biological sample.

According to the foregoing structure, since a solution containing a biological sample can be discharged upon selecting a discharge means having a normal discharge status, the biological sample may be reliably and stably spotted on a solid phase. Further, since a large variety of biological samples can be discharged approximately simultaneously, faster preparation of the microchips may be realized.

The dispensing device according to the present invention comprises: an electrode substrate having a plurality of separate electrodes formed in correspondence with each of a plurality of pressurized chambers to be filled with a solution containing a biological sample; a pressurized chamber substrate, disposed so as to face the electrode substrate in a minute gap, having a discharge mechanism for adjusting the pressure inside the pressurized chamber by mechanical displacement of an elastically deforming diaphragm with an electrostatic force corresponding to a potential difference with the separate electrodes, and discharging the solution from a nozzle hole; a drive pulse generation circuit for applying a drive voltage pulse of a prescribed waveform between the diaphragm and the separate electrodes in order to discharge the solution from the nozzle hole; a drive current detection circuit for detecting a drive current flowing between the diaphragm and separate electrodes when the drive voltage pulse is applied; discrimination means for discriminating the existence of a defective discharge of the solution based on the drive current detected with the drive current detection circuit; and control means for selecting the discharge means in which the discharge status is not defective as a result of discriminating the defective discharge with the discrimination means, and performing discharge control of the solution containing the biological sample.

According to the present invention, attention was focused on the point of the drive current flowing between the diaphragm and separate electrodes changing as a result of a defective discharge, and, by providing a means for detecting such drive current, it is possible to discriminate the defective discharge of the respective discharge mechanisms.

Preferably, the discrimination means discriminates the existence of a defective discharge of the solution based on a current waveform of the detected drive current.

Since the waveform of the detected drive current differs between where the discharge status is normal and where it is abnormal, a defective discharge can be discriminated by detecting the difference in the two waveforms.

Preferably, the discrimination means discriminates the existence of a defective discharge of the solution based on a peak current value of the detected drive current.

Since the peak current value of the detected drive current differs between where the discharge status is normal and where it is abnormal, a defective discharge can be discriminated by detecting the difference in the two peak current values.

Preferably, the discrimination means discriminates the existence of a defective discharge of the solution based on a differential waveform of the detected drive current.

Since the change in drive current can be sensitively detected by employing the differential waveform of the detected drive current, accuracy of the defective discharge discrimination can be secured.

Preferably, the discrimination means performs the discrimination as a result of whether a peak waveform of the differential waveform appears on the positive side two consecutive times.

When a defective discharge occurs, since the peak waveform has a characteristic of appearing on the positive side two consecutive times to the differential waveform of the detected drive current, a defective discharge can be discriminated by employing such characteristic.

Preferably, the discrimination means performs the discrimination as a result of whether a positive-side peak waveform appears on the differential waveform immediately prior to the falling edge of the detected drive current waveform.

When a defective discharge occurs, since a positive-side peak waveform has a characteristic of appearing on the differential waveform immediately prior to the falling edge of the detected drive current waveform, a defective discharge can be discriminated by employing such characteristic.

Preferably, the drive current detection circuit detects the drive current during the period in which the diaphragm elastically deforms toward the separate electrodes or during the period in which the diaphragm elastically deforms away from the separate electrodes.

During the foregoing periods, since changes in the detected drive current are significant, this is favorable in discriminating a defective discharge.

Preferably, the discrimination means performs the discrimination by comparing the detected drive current with a pre-stored drive current to be employed upon a normal drive.

Since the waveform of the detected drive current differs between where the discharge status is normal and where it is abnormal, a defective discharge can be discriminated by detecting the difference in the two waveforms.

Preferably, the discrimination means performs the discrimination by comparing the synthesized current of the detected drive current obtained upon applying a drive voltage pulse between a plurality of sets of diaphragms and separate electrodes with a pre-stored synthesized current of a drive current to be employed upon normally driving a plurality of sets of diaphragms and separate electrodes.

According to the foregoing structure, a defective discharge of a plurality of discharge mechanisms can be discriminated at the same time.

The dispensing device according to the present invention comprises: an electrode substrate having a plurality of separate electrodes formed in correspondence with each of a plurality of pressurized chambers to be filled with a solution containing a biological sample; a pressurized chamber substrate, disposed so as to face the electrode substrate in a minute gap, having a discharge mechanism for adjusting the pressure inside the pressurized chamber by mechanical displacement of an elastically deforming diaphragm with an electrostatic force corresponding to a potential difference with the separate electrodes, and discharging the solution from a nozzle hole; inspection pulse output means for applying an inspection pulse of a trapezoid waveform having a smooth rising edge gradient between the diaphragm and the separate electrodes; a current detection circuit for detecting the excess current flowing between the diaphragm and separate electrodes when the inspection pulse is applied; discrimination means for discriminating the existence of a defective discharge of the solution based on the drive current detected with the current detection circuit; and control means for selecting the discharge means in which the discharge status is not defective as a result of discriminating the defective discharge with the discrimination means, and performing discharge control of the solution containing the biological sample.

According to the foregoing structure, as a result of employing the inspection pulse of a trapezoid waveform having a smooth rising edge gradient, changes in the excess current flowing between the diaphragm and separate electrodes can be enlarged between where the discharge status is normal and where it is abnormal, and a defective discharge may thereby be detected sensitively.

The dispensing device according to the present invention comprises: an electrode substrate having a plurality of separate electrodes formed in correspondence with each of a plurality of pressurized chambers to be filled with a solution containing a biological sample; a pressurized chamber substrate disposed so as to face the electrode substrate in a minute gap for adjusting the pressure inside the pressurized chamber by mechanical displacement of an elastically deforming diaphragm with an electrostatic force corresponding to a potential difference with the separate electrodes, and discharging the solution from a nozzle hole; optical detection means for optically detecting whether the solution has been discharged from the nozzle hole upon activating the discharge mechanism; discrimination means for discriminating the existence of a defective discharge of the solution from the detection results of the optical detection means; and control means for selecting the discharge means in which the discharge status is not defective as a result of discriminating the defective discharge with the discrimination means, and performing discharge control of the solution containing the biological sample.

According to the foregoing structure, a defective discharge can be detected optically.

Preferably, the optical detection means is structured from a laser light source and a light reception sensor, and detects whether the solution has been discharged from the change in received light intensity of a laser beam transmitted through the solution discharged as a droplet from the nozzle hole.

According to the foregoing structure, a defective discharge can be detected optically based on the received light intensity of the light reception sensor.

Preferably, the optical means is structured from a CCD sensor, and optically detects the solution discharged as a droplet from the nozzle hole.

Preferably, further provided is recovery means for recovering the discharge mechanism, which resulted in a defective discharge, to a normal state. Suction means of a solution containing a biological sample is suitable for such recovery means.

According to the foregoing structure, degeneration and coagulation of the biological sample, and mixing of air bubbles into the pressurized chamber, which may cause a defective discharge, may be prevented, and recovery to a normal discharge status can be enabled thereby.

By employing protein or nucleic acid as the biological sample, microarrays such as a protein chip or a DNA chip can be prepared.

The method of detecting a defective discharge of a solution containing a biological sample according to the present invention is a method of detecting a defective discharge of a solution in a discharge mechanism for adjusting the pressure inside the pressurized chamber by mechanical displacement of an elastically deforming diaphragm, which is disposed so as to face an electrode substrate in a minute gap having a plurality of separate electrodes formed in correspondence with each of the plurality of pressurized chambers to be filled with a solution containing a biological sample, with the electrostatic force corresponding to the potential difference with the separate electrodes, and discharging the solution from a nozzle hole, comprising the steps of: applying a drive voltage pulse of a prescribed waveform between the diaphragm and the separate electrodes in order to discharge the solution from the nozzle hole; detecting a drive current flowing between the diaphragm and separate electrodes when the drive voltage pulse is applied; and discriminating the existence of a defective discharge of the solution based on the detected drive current.

According to the foregoing method, attention was focused on the point of the drive current flowing between the diaphragm and separate electrodes changing as a result of a defective discharge, and, by detecting such drive current, it is possible to discriminate the defective discharge of the respective discharge mechanisms.

The method of detecting a defective discharge of a solution containing a biological sample according to the present invention is a method of detecting a defective discharge of a solution in a discharge mechanism for adjusting the pressure inside the pressurized chamber by mechanical displacement of an elastically deforming diaphragm, which is disposed so as to face an electrode substrate in a minute gap having a plurality of separate electrodes formed in correspondence with each of the plurality of pressurized chambers to be filled with a solution containing a biological sample, with the electrostatic force corresponding to the potential difference with the separate electrodes, and discharging the solution from a nozzle hole, comprising the steps of: applying an inspection pulse of a trapezoid waveform having a smooth rising edge gradient between the diaphragm and the separate electrodes; detecting an excess current flowing between the diaphragm and separate electrodes when the inspection pulse is applied; and discriminating the existence of a defective discharge of the solution based on the detected drive current.

According to the foregoing method, as a result of employing the inspection pulse of a trapezoid waveform having a smooth rising edge gradient, changes in the excess current flowing between the diaphragm and separate electrodes can be enlarged in the case where the discharge status is normal and in the case where it is abnormal, and a defective discharge may thereby be detected sensitively.

The method of detecting a defective discharge of a solution containing a biological sample according to the present invention is a method of detecting a defective discharge in discharge means for discharging a solution containing a biological sample, comprising the steps of: optically detecting whether the solution has been discharged upon activating the discharge means; and discriminating the existence of a defective discharge of the solution from the detection results.

According to the foregoing method, a defective discharge can be detected optically.

The dispensing method according to the present invention comprises the steps of: discriminating a defective discharge of a discharge mechanism with a method according to present invention described above as a preparatory step for spotting a solution containing a biological sample on a substrate; and selecting a discharge mechanism in which the discharge status is not defective and spotting the solution on the substrate.

According to the foregoing method, since the discrimination of a defective discharge is performed as a preparatory step for the spotting of the biological sample and spotting is thereafter performed with a discharge mechanism of a normal discharge status, the biological sample may be reliably and stably spotted on a solid phase.

Preferably, a microarray is prepared by spotting the solution containing a biological sample on an array.

According to the foregoing method, cross contamination is suppressed as much as possible, and a high quality microarray can be prepared thereby.

Preferably, a protein chip is prepared by employing a variety of proteins as the biological sample.

According to the foregoing method, a high quality protein chip suitable for proteomics research can be prepared.

DETAILED DESCRIPTION OF THE PREFERRED EMBODIMENTS

Embodiment 1

Figure 1:
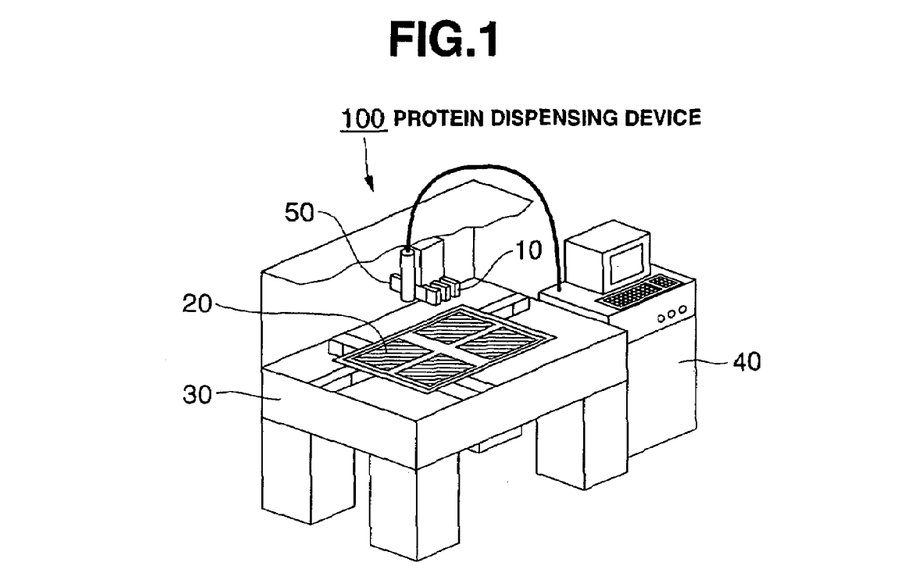
FIG. 1 is a structural diagram of the protein dispensing device.

FIG. 1 is a structural diagram of the protein dispensing device in the present embodiment.

This device 100 is structured by having a microdispenser array 10 for approximately simultaneously discharging foreign protein, a protein chip 20 in which a large variety of proteins has been spotted in a high density array shape, a stage 30 for mounting the protein chip 20, a drive control device 40 for relatively moving the microdispenser array 10 and protein chip 20 and performing discharge control of the protein solution, and a CCD sensor 50 for optically detecting the discharge status of the protein solution on the protein chip 20.

Figure 2:
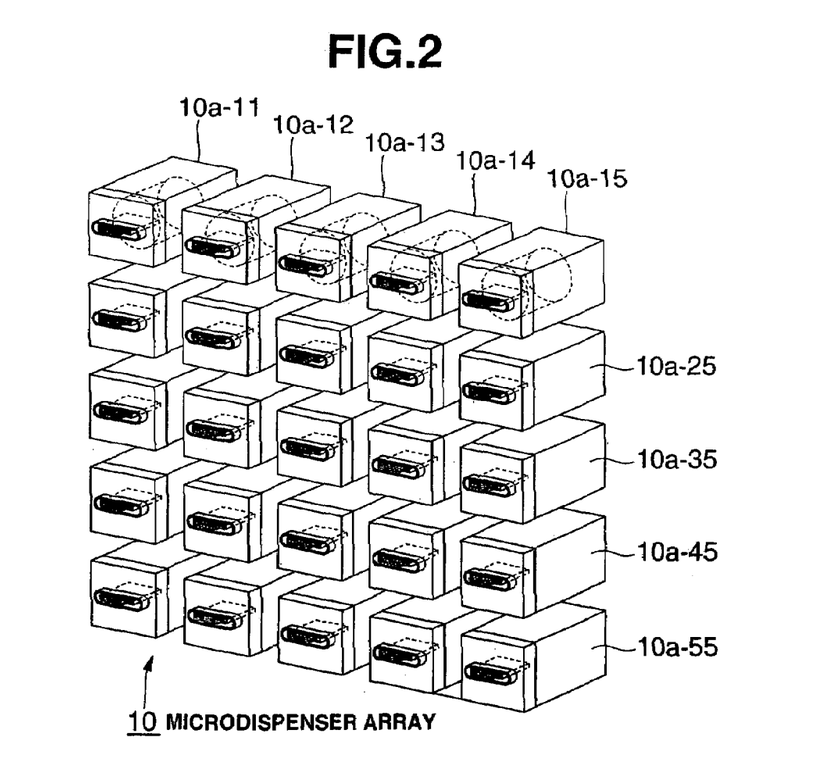
FIG. 2 is a structural diagram of the microdispenser array.

FIG. 2 is a structural diagram of the microdispenser array 10.

This array 10 has a structure in which microdispensers 10$a$-$ij$ are arranged in a matrix shape at a position of i lines×j columns. In FIG. 2, exemplified is a structure of 5 lines and 5 columns. Each of the microdispensers 10$a$-$ij$ is structured to mutually discharge different protein solutions. The number of lines and columns of the array 10 and the total number of microdispensers 10$a$-$ij$ are suitably determined in accordance with the type and discharge amount of protein solution to be spotted. For example, for protein solutions to be discharged in large amounts, the microdispenser array 10 is structured such that the plurality of microdispensers 10$a$-$ij$ contains the same type of protein solution. Although not illustrated in FIG. 2, each of the microdispensers 10$a$-$ij$ has a stopper mechanism for determining the relative positioning of adjacent microdispensers 10$a$-$(i\pm1)(j\pm1)$, and designed to be housed in a prescribed storage container such that the pitch among the dispensers becomes an equal spacing.

Figure 3:
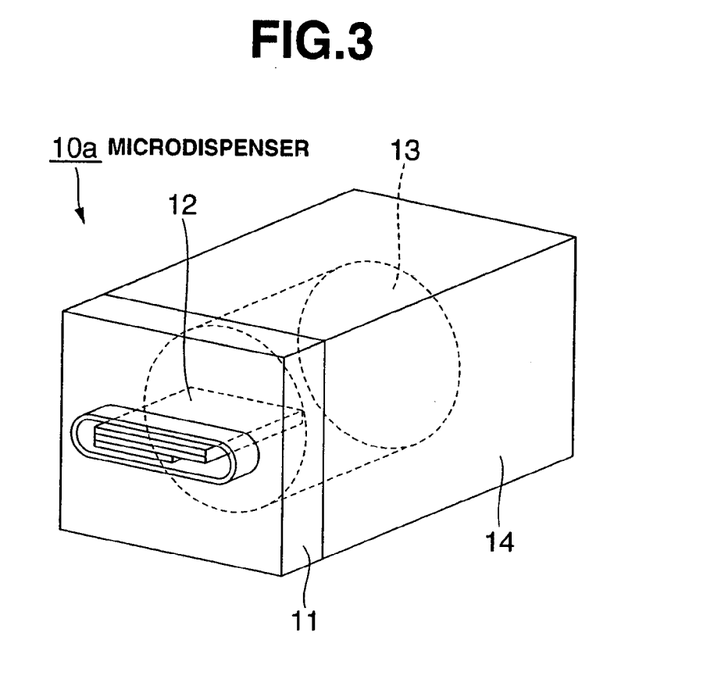
FIG. 3 is a structural diagram of the microdispenser.
Figure 4:
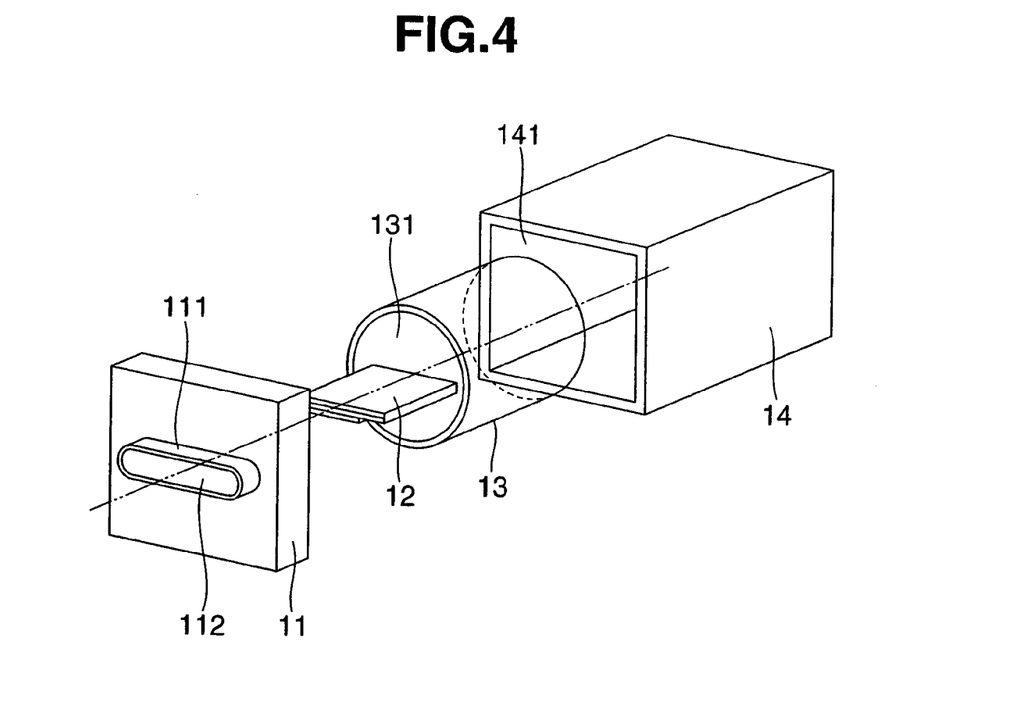
FIG. 4 is an exploded perspective view of the microdispenser.

FIG. 3 is a structural diagram of the microdispenser 10$a$, and FIG. 4 is an exploded perspective view of the microdispenser 10$a$. For convenience of explanation, a perspective projection is partially employed in the drawings.

The microdispenser 10$a$ is structured by having a cover 11, a head chip 12, a tank 13 and a case 14. A discharge outlet 111 having an opening 112 for discharging a protein solution is formed on the cover 11. The head chip 12 is of a laminate substrate structure having an electrostatic head structure, and is structured to discharge a solution containing protein stored inside the hollow portion 131 of the tank 13. Capacity of the hollow portion 131 is, for instance, 1 ml. In order to stably discharge a solution containing protein, it is desirable that the viscosity of the solution to be filled in the hollow portion 131 be within the range of 1 mNs/m² to 20 mNs/m², and surface tension of 30 mN/m to 50 mN/m. The case 14 houses the head chip 12 and tank 13 within the hollow portion 131, and the cover 11 is adhered thereto so as to block the opening of the hollow portion 131.

As the structural material of the cover 11 and case 14, there is no particular limitation so as long as the material is easy to mold and has adequate strength, and possesses corrosion resistance against a solution containing protein, and, for example, synthetic resin such as polyvinyl chloride or a glass material may be suitably employed. Moreover, as the structural material of the tank 13, there is no particular limitation so as long as the material possesses corrosion resistance against the solution to be filled and has adequate elasticity for applying a moderate internal pressure to the filled solution and supplying the solution to the head chip 12, and, for example, isobutylene-isoprene rubber or the like may be suitably employed. In order to stably supply the solution to the head chip 12, the solution must be housed inside the hollow portion 131 under a pressure (negative pressure) smaller than the atmospheric pressure. Nevertheless, by structuring the tank 13 with isobutylene-isoprene rubber, since permeability of the solution and vapor will be low, it is possible to satisfy a prescribed pressure condition while preventing the penetration of gas and vapor inside the tank and outflow of the solution from the tank. Further, as the structural material of the tank 13, it is preferable to eliminate in advance any material that may degenerate the housed protein.

Incidentally, although not illustrated, the tank 13 is hermetically sealed while having a filling hole for filling the solution containing protein and a packing for hermetically sealing portions other than the supply port for supplying the solution to the head chip 12. As a result of sealing the filling hole of the solution and adopting a disposable structure for the microdispenser 10a, cross contamination with other biological molecules can be effectively prevented.

Figure 5:
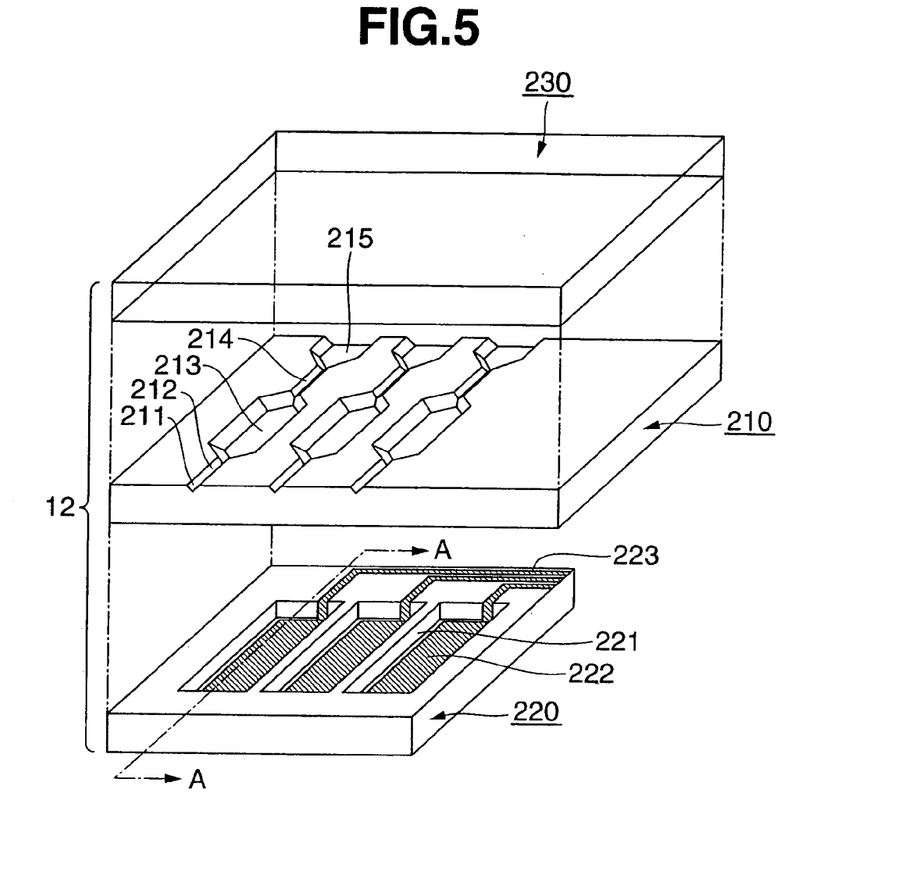
FIG. 5 is an exploded perspective view of the head chip.
Figure 6:
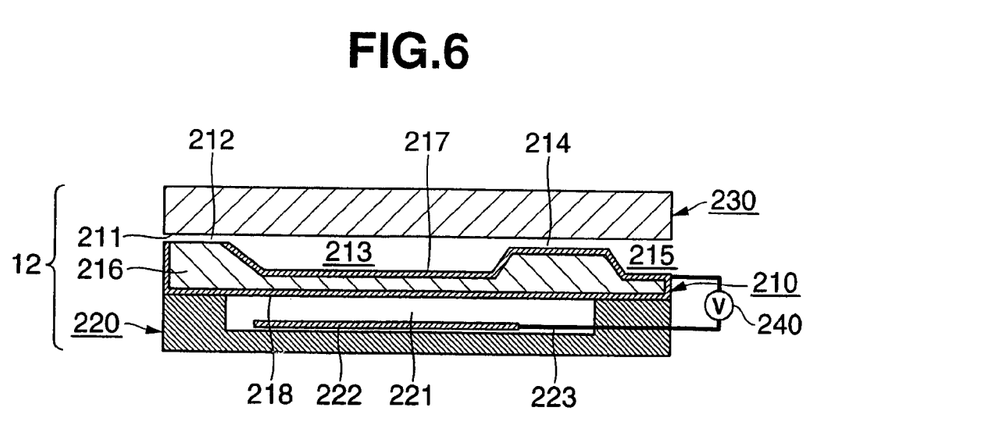
FIG. 6 is a cross section of the head chip.

FIG. 5 is an exploded perspective view of the head chip 12, and FIG. 6 is the A-A cross section depicted in FIG. 5.

The head chip 12 has a laminated structure in the direction of sandwiching the front face and rear face of the pressurized chamber substrate 210, respectively, toward the radial thickness direction with the electrode substrate 220 and the upper substrate 230. The pressurized chamber substrate 210 is structured by having a flow path configuration including a nozzle 211, a nozzle groove 212, a pressurized chamber 213, a supply groove 214 and a reservoir 215, and is obtained by etch-forming a silicon substrate in a prescribed pattern of a concave shape. As the silicon substrate to be employed as the pressurized chamber substrate 210, a monocrystal silicon substrate, a polycrystal silicon substrate or a SOI substrate may be used. When the plane direction of the silicon substrate is set to (110) and anisotropic etching is performed with a potassium hydroxide solution, the pressurized chamber 213 and reservoir 215 having a boat-shaped cross section are formed. The pressurized chamber substrate 210, as illustrated in FIG. 6, has a structure of being covered by a silicon oxide film 217 deposited by performing the thermal oxidation method, sputtering method, deposition method, ion plating method, sol-gel method, CVD method and so on to the surface of the silicon substrate 216. As a result of covering the surface of the pressurized chamber substrate 210 with the silicon oxide film 217, affinity with biological samples such as protein and antigens/antibodies can be improved, and this is suitable as a protein dispenser head. Moreover, the silicon oxide film 217 also has high affinity with nucleic acids of DNA, RNA, PNA and the like, and this is further suitable as a dispenser head for other biological samples such as DNA described later.

Although the suitable distance of the nozzle pitch will significantly differ according to the contact angle of the protein solution and nozzle head, surface tension of the protein solution, among other factors, there is no particular limitation so as long as it is a spacing in which cross contamination will not occur easily, and, for example, roughly 0.5 mm is a preferable spacing. Further, with the example shown in FIG. 5, although exemplified is a case of adopting a flow path structure of a 3-nozzle system per chip, it is not limited thereto, and an optimum flow path structure may be determined based on the area of the pressurized chamber substrate 210 or the physical characteristics (viscosity, surface tension, contact angle) of the protein solution.

The electrode substrate 220 is a substrate for housing separate electrodes (counter electrodes) 222 for applying voltage in an electrostatic head structure, and is structured from the likes of a borosilicate glass substrate. Since the borosilicate glass substrate contains abundant alkali ion and the coefficient of thermal expansion approximately coincides with a silicon substrate, this is preferable for anode connection with the pressurized chamber substrate 210. Since this anode connection does not use an adhesive, aseptic connection with the biological sample is enabled. Moreover, when affixed to the pressurized chamber substrate 210, a concave portion 221 is formed at a position corresponding to the respective pressurized chambers 213. Separate electrodes 222 formed from a conductive thin film are deposited on the bottom face of the respective concave portions 221, and are in conduction with the power source 240 via the wiring 223. As the separate electrodes, for instance, ITO or the like deposited to have a film thickness of roughly 0.1 μm with the sputtering method may be preferably employed. The minute gap between the separate electrodes 222 and the pressurized chamber substrate 210 is preferably selected to be a distance enabling the discharge of a solution with an electrostatic drive, and, for example, roughly 0.2 μm is a preferable distance.

When an orthogonal wave having an amplitude of 0V to 35V is applied between the pressurized chamber substrate 210 functioning as the common electrode and the respective separate electrodes 222, an electrostatic force will work between the bottom face of the pressurized chamber 213 and the separate electrodes 222, the bottom face of the pressurized chamber 213 will slightly bend toward the concave portion 221, and cause elastic deformation. Here, the bottom face of the pressurized chamber 213 functions as the diaphragm 218. Next, when the amplitude of the orthogonal wave is set to 0V, the electrostatic force will be released, bending of the diaphragm 218 will be restored to its original state, and the pressure inside the pressurized chamber 213 will be instantaneously increased. Then, a solution containing protein will be discharged from the nozzle 211. The diaphragm 218 deformed inside the pressurized chamber 213 will once again bend toward the concave portion 221 as a result of its repulsive force, and one-shot worth of protein solution will be re-supplied from the reservoir 215 into the pressurized chamber 213.

Incidentally, as the structural material of the upper substrate 230, a glass substrate such as borosilicate glass is preferable upon giving consideration to a certain degree of rigidity, corrosion resistance against the solution containing protein, cost, visibility and so on.

Figure 11:
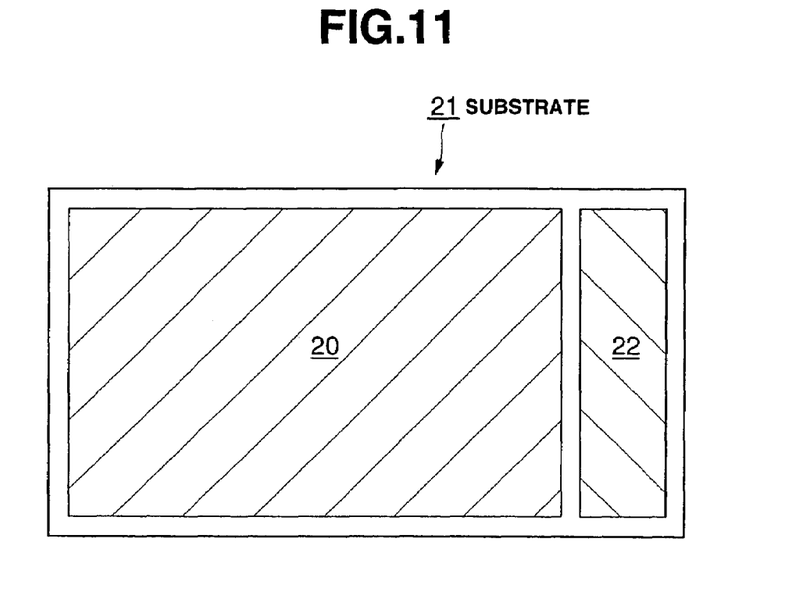
FIG. 11 is an explanatory diagram of the protein chip.

In the present embodiment, as a preparatory step of preparing the protein chip 20, a nozzle 211 of a favorable discharge status is selected upon driving the microdispenser array 10 and performing a trial shoot of the protein solution in a dummy area 22. Thus, as shown in FIG. 11, a dummy area 22 for the trial shoot is provided on the substrate for preparing the protein chip 20. As a means for discriminating the quality of the discharge status of the solution, although various methods may be considered, in the present embodiment, discrimination will be performed based on the drive current waveform upon the protein solution being discharged from the head chip 12. If a nozzle 211 of a favorable discharge status has been selected, the protein solution is discharged from such selected nozzle 211 to the substrate 21 in order to prepare the protein chip 20.

Figure 7:
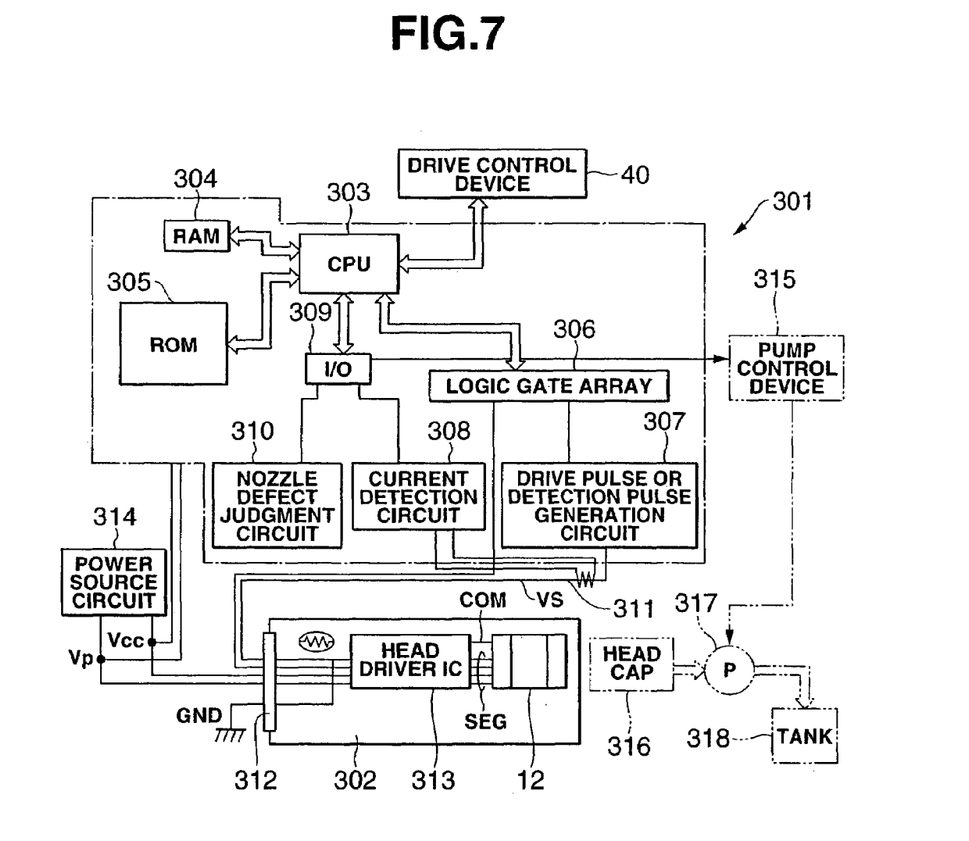
FIG. 7 is a structural diagram of the head chip control circuit.

FIG. 7 is a structural diagram of the drive control circuit for controlling the drive of the head chip 12.

This control circuit has, as its principal components, a control unit 301 structured around a CPU 303, and a circuit substrate 302 structured around the head chip 12. The control unit 301 is structured by having a CPU 303, a RAM 304, a ROM 305, a logic gate array 306, a drive pulse generation circuit 307, a drive current detection circuit 308, an I/O interface 309, and a nozzle defect judgment circuit 310. The circuit substrate 302 is structured by having a connector 312, a head driver IC 313 and a head chip 12.

Figure 9:
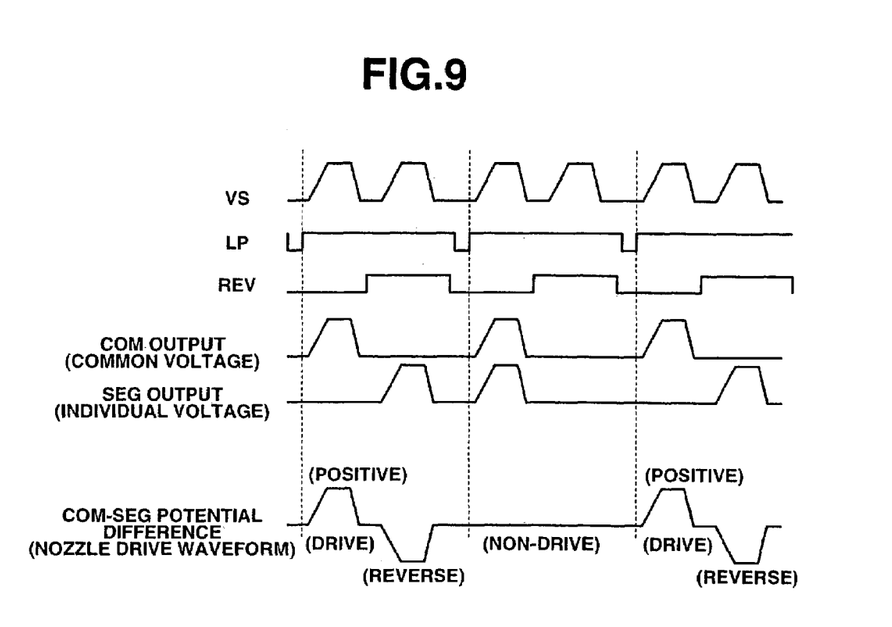
FIG. 9 is a waveform chart of the various drive control signals of the head chip.

When the CPU 303 receives head drive information output from the drive control device 40 via the bus, it uses the RAM 304 as the work area and generates a control signal for driving the head chip 12 in accordance with a program stored in the ROM 305. This drive control signal is supplied to the head driver IC 313 via the connector 312 as a drive control signal corresponding to the head drive information via the logic gate array 306 and drive pulse generation circuit 307. Moreover, as shown in FIG. 9, a reference drive voltage pulse signal VS, a control signal LP, and an inversion control signal REV are respectively supplied to the head driver IC 313. Each of these signals is generated with the drive pulse generation circuit 307 and the logic gate array 306.

At the head driver IC 313, based on the drive voltage Vp supplied from each of the foregoing signals and the power source circuit 314, a drive voltage pulse signal to be applied to the common electrode (pressurized chamber substrate 210) is output from the output terminal COM thereof, and a drive voltage to be applied to the separate electrodes 222 provided inside the pressurized chamber 213 is output from the output terminal SEG. Difference between the COM output and SEG output (COM-SEG potential difference output) becomes the drive voltage, elastically deforms the diaphragm 218 provided to the respective pressurized chambers 213, and adjusts the internal pressure of the pressurized chamber 213. Upon discharging a solution, while discharging a protein solution by providing a prescribed potential difference to the COM output and SEG output on the one hand, the potential difference is set to 0V when a solution is not to be discharged.

FIG. 9 shows the respective voltage waveforms of the reference drive voltage pulse signal VS, control signal LP, inversion control signal REV, COM output, SEG output, and COM-SEG potential difference output. In the illustrated example, anticipated is a case of forming one spot with two shots (two discharges). The inversion signal REV is a signal for reversing the SEG output for performing two consecutive shots. As described above, as a result of AC-driving the head chip 12, variations in the electrostatic force pursuant to the accumulation of the residual charge between the separate electrodes 222 and the common electrode can be suppressed, and favorable discharge characteristics can be secured.

Figure 10:
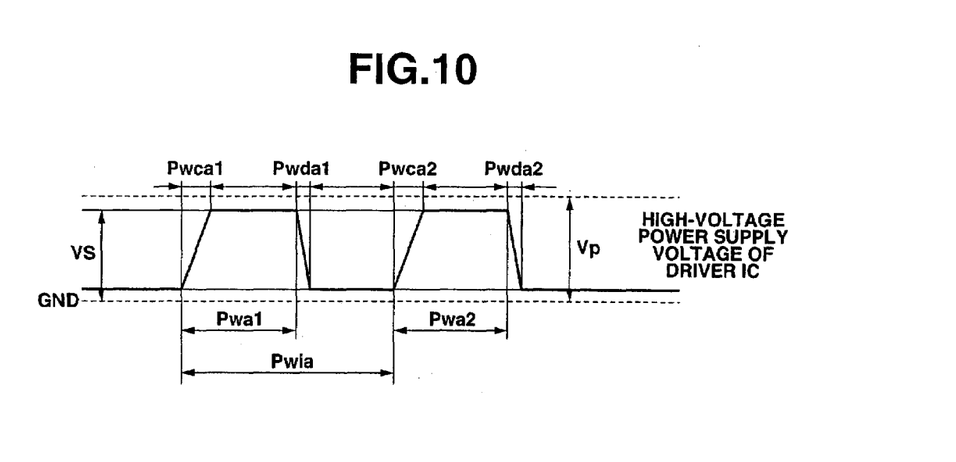
FIG. 10 is a waveform chart of the reference drive voltage pulse signal.

FIG. 10 shows the voltage waveform of the reference drive voltage pulse signal VS upon forming one spot with two shots. As illustrated in FIG. 10, one-cycle worth of the voltage waveform of the reference drive voltage pulse signal VS is Pwia; the pulse width of the charge portion rising at a fixed gradient is Pwca1, Pwca2; the pulse width of the discharge portion falling at a gradient steeper than the charge portion after being retained at a fixed voltage after the rising edge is Pwda1, Pwda2, and the pulse width from the starting point of the charge portion up to the starting point of the discharge portion is Pwa1, Pwa2.

Here, when returning to FIG. 7 and continuing the explanation, the control circuit 301 has a drive current detection circuit 308 for detecting the drive current I flowing in the signal supply line 311 of the reference drive voltage pulse signal VS. When the drive current detection circuit 308 detects the drive current flowing between the separate electrodes 222 and the common electrode, it supplies the value of the detected drive current to the nozzle defect judgment circuit 310. The nozzle defect judgment circuit 310 discriminates whether there is a defective discharge of a solution in the respective nozzles 211 based on the detected drive current.

Figure 8A:
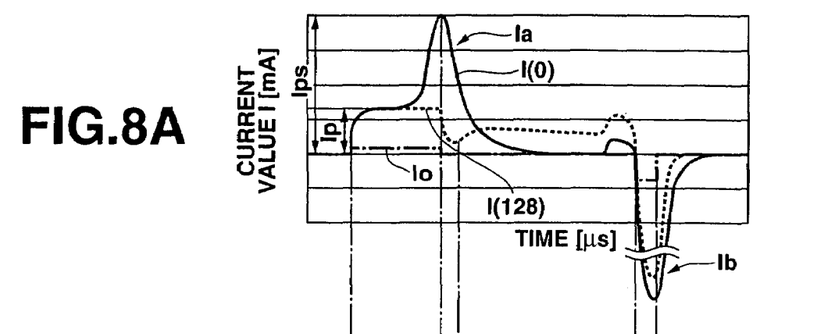
FIG. 8 is a diagram for explaining the waveform change of the detected drive current.
Figure 8B:
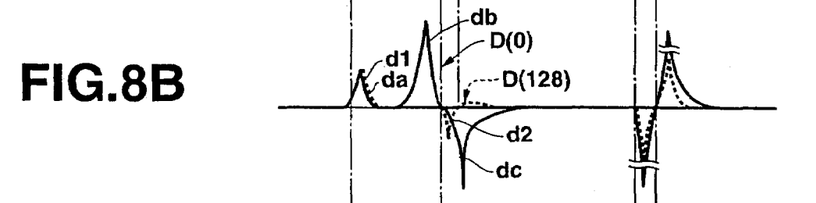
Figure 8C:
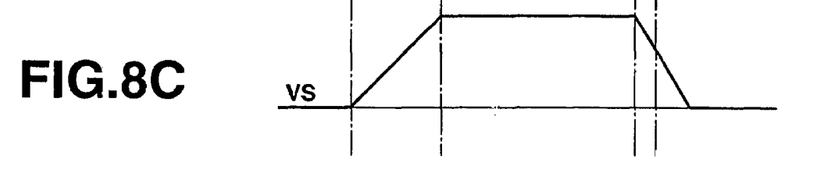

FIG. 8 shows the waveform of the drive current I detected upon applying one-pulse worth of the reference drive voltage pulse signal VS. Specifically, in FIG. 8(a), in a case where the head chip 12 has a total of 128 nozzles 211, the drive current waveform detected when all nozzles 211 are not driven is displayed as $I_0$, the drive current waveform detected upon the protein solution being normally discharged from all nozzles 211 in a case where all nozzles 211 are driven is displayed as I (128), and the drive current waveform detected upon the protein solution not being discharged from all nozzles 211 in a case where all nozzles 211 are driven is displayed as I (0). FIG. 8(c) shows a voltage waveform of one-pulse worth of the reference drive voltage pulse signal VS.

As evident when comparing these drive current waveforms $I_0$, I (128) and I (0), the drive current waveform I (0) detected when the protein solution is not discharged from the nozzle 211 differs from both the drive current waveform $I_0$ detected when the nozzle 211 is not driven and the drive current waveform I (128) detected when the solution is normally discharged from all nozzles 211. Further, the drive current waveform I (0) has a larger absolute value of the peak current value for the peak waveform portion in comparison to the drive current waveform I (128). To explain this point in detail, the peak of the drive current waveform I appears at the vicinity of the ending point of the rising edge and the vicinity of the ending point of the falling edge of the reference drive voltage pulse signal VS. In other words, when the reference drive voltage pulse signal VS is applied between the separate electrodes 222 and the common electrode, the diaphragm 218 begins to elastically deform as a result of the electrostatic suction force arising therebetween, is thereafter sucked in by the separate electrodes 222, and is adsorbed to the surface thereof. The capacitance between the diaphragm 218 and the separate electrodes 222 changes in inverse proportion to the gap thereof, and the drive current I changes in proportion to the time rate of the capacitance. Therefore, since the capacitance increases drastically at the rising edge of the reference drive voltage pulse signal VS, the drive current I will rise in the positive direction pursuant thereto. Contrarily, during the falling edge of the reference drive voltage pulse signal VS, the electrostatic suction force will decrease, and the diaphragm 218 adsorbed to the separate electrodes 222 will be released from the separate electrodes 222 as a result of the elastic restoration force. Thus, the drive current I will rise in the negative direction.

Here, when air bubbles get mixed into the tank 13 and discharge of the solution is defective or impossible, since the filling ratio of the protein solution inside the hollow portion 131 is low, the oscillation speed of the diaphragm 218 will increase for such portion. As a result, the rate of change of capacitance will increase. Thus, peak waveforms Ia and Ib appear in the drive current I at the point the diaphragm 218 is adsorbed to the separate electrodes 222 and at the point when it is released from the separate electrodes 222 as shown with the drive current waveform I (0) depicted in FIG. 8(a). And, when comparing these with the peak waveform portion corresponding to the drive current waveform I (128), in addition to becoming a steeper waveform, the absolute value of the peak current value will significantly differ. With the nozzle defect judgment circuit 310, attention is focused on changes in the characteristics of the drive current waveforms described above, and the existence of a defective discharge of a solution is judged thereby.

Incidentally, in FIG. 8, although the drive current wave I (128) and drive current waveform I (0) were illustrated in order to compare the difference of the drive current waveform during a normal discharge of the solution and the drive current waveform during a defective discharge of the solution, it has been confirmed that the relation of the two has a small variation between a drive current waveform obtained from a single defective nozzle, but may be similarly applied thereto. Further, even in cases where the discharge of a solution becomes defective from the degeneration or coagulation of the protein, and not from air bubbles getting mixed into the tank 13, the existence of a defective discharge of the solution can be judged by detecting the change in characteristics of the drive current waveform.

As a specific discrimination means for discriminating a defective discharge of a solution, although various methods may be considered, for example, by pre-storing the peak waveform of the drive current of the nozzle capable of normally discharging a solution in a memory and comparing such peak waveform and the peak waveform of the detected drive current I, a defective discharge of the solution can be judged when the difference of the two exceeds a predetermined threshold value. The peak waveform portion to be compared may be either the peak waveform Ia on the positive side or the peak waveform Ib on the negative side. Further, with this kind of discrimination method, the existence of a defective discharge may also be individually discriminated by sequentially applying a drive voltage pulse to a plurality of nozzles, and, the structure may also be such that the synthesized waveform in which synthesized is a drive current obtained upon applying the drive voltage pulse to all nozzles simultaneously and the synthesized waveform in which synthesized is a drive current obtained upon simultaneously driving the normal nozzle pre-stored in the memory are compared, and a defective discharge may be judged when the difference of the two exceeds a predetermined threshold value.

As another discrimination method, a defective discharge may be discriminated based on the peak waveform appearing on the differential waveform obtained by performing differential processing to the detected drive current waveform I. FIG. 8(b) shows the differential waveform D (128) and D (0) in which differential processing was performed to the drive current waveforms of I (128) and I (0). With the differential waveform D (128), a peak waveform d1 on the positive side and a peak waveform d2 on the negative side appear at the rising edge and falling edge of the current waveform of I (128). Contrarily, with the differential waveform D (0), since the peak waveform appears after the current waveform of I (0) initially rising and thereafter once again rises in the same direction, peak waveforms da, db on the positive side appear consecutively, and the peak waveform dc on the negative side appears immediately thereafter. In light of this kind of difference in the characteristics of the differential waveforms, the existence of a defective discharge can be discriminated based on whether a peak waveform appears consecutively on the positive side. Or, immediately prior to the falling edge of the detected drive current waveform I, a defective discharge can be discriminated by whether a positive-side peak waveform can be obtained on the differential waveform.

The discriminating method of a defective discharge based on the differential waveform is advantageous in that it is of a higher sensitivity in comparison to discrimination methods based on the peak current waveform or peak current value of the detected drive current waveform I. Moreover, even in the foregoing case, the judgment of a defective discharge may be made by individually discriminating the defective discharge while applying a drive voltage pulse in order to the respective nozzles, and, in addition, discrimination may also be made based on the differential waveform obtained by differentiating the synthesized waveform in which synthesized is a drive current obtained upon applying a drive voltage pulse to all nozzles simultaneously.

Further, in order to discriminate the existence of a defective discharge, a structure may also be adopted in which applied is an inspection pulse having a different waveform than the reference drive voltage pulse signal VS normally used to drive the head chip. In other words, since the waveform difference of the excess current waveform detected in the normal state and abnormal state is slight, it is preferable to apply the inspection pulse so as to expand the waveform difference of such current waveforms. In order to achieve the above, a smooth trapezoid waveform of a rising edge gradient may be applied as the inspection pulse. That is to say, the pulse width Pwia depicted in FIG. 10 may be lengthened, or the amplitude of the inspection pulse may be shortened. When the voltage amplitude of the inspection pulse is reduced, although the diaphragm 218 will be adsorbed to the separate electrodes 222 when air bubbles exceeding a prescribed amount get mixed into the pressurized chamber 203, it will be possible to generate an electrostatic force having an intensity that will not make the diaphragm 218 be adsorbed to the separate electrodes 222 in a state with no air bubbles. By employing the inspection pulse capable of realizing this kind of state, the difference in the shapes of the excess current waveform during a normal state and the excess current waveform during an abnormal state will become even clearer, and the existence of a defective discharge can be detected with high sensitivity.

Enablement of a droplet discharge may also be judged with a nozzle defect judgment circuit 310 by outputting as a sine waveform an amplitude probe voltage waveform of roughly 5V from the drive pulse generation circuit 307 depicted in FIG. 7, increasing and sweeping the frequency of the probe voltage waveform from, for example, 1 kHz to 100 kHz in 1 kHz intervals, detecting the current value against the frequency of the probe voltage waveform with the drive current detection circuit 308, and detecting the resonance frequency of the diaphragm 218 of the head chip 12. As a result of detecting the current with the drive current detection circuit 308, it will be possible to detect the frequency, in which the current value will become highest, as the resonance frequency. Here, if air bubbles, which may cause a defective discharge of droplets, get mixed into the pressurized chamber 213, the resonance frequency will become higher than normal, and, when protein coagulation in the vicinity of the nozzle 211 causes a defective discharge, the resonance frequency will become lower than normal. For instance, in a case where the resonance frequency is 33 kHz, enablement of the droplet discharge is judged with the nozzle defect judgment circuit 310 wherewith the normal discharge is 25 kHz or higher and 45 kHz or lower.

With these methods, it is possible to enhance the precision of detection, and thereby provided is a detection method suitable for an electrostatic system having a structure where the current value varies significantly as a result of the capacitance changing due to the amplitude by oscillation.

Incidentally, in FIG. 7, the head driver IC 313 may be omitted. If the head driver IC 313 is omitted, it will be possible to detect the current directly input/output to and from the head chip 12, and the precision of detection may thereby be improved.

According to the present embodiment, as indicated with the imaginary line depicted in FIG. 7, it is preferable to add a mechanism for recovering the defective discharge of the nozzle. In FIG. 7, the pump control circuit 315 operates the liquid suction pump 317, sucks the protein solution from the nozzle 211 of a defective discharge via a head cap 316 capable of being capped on the nozzle head, and stores this in the tank 318 for waste solution. Since there is a possibility that the air bubbles got mixed into the pressurized chamber 213 or the protein become degenerated or coagulated regarding the nozzle 211 of a defective discharge, such defective discharge can be resolved pursuant to the foregoing suction operation.

As described above, according to the present embodiment, since a protein chip is prepared upon discriminating a defective discharge from the drive current waveform of the nozzle and selecting a nozzle having a favorable discharge status, a large variety of proteins may be stably discharged, and the preparation of protein chips may be sped up. Further, as a result of the discharge characteristics of the protein solution becoming stable, the generation of cross contamination caused by the scattering of droplets can be effectively suppressed, and a high quality protein chip may be prepared as a result thereof.

Embodiment 2

Figure 12:
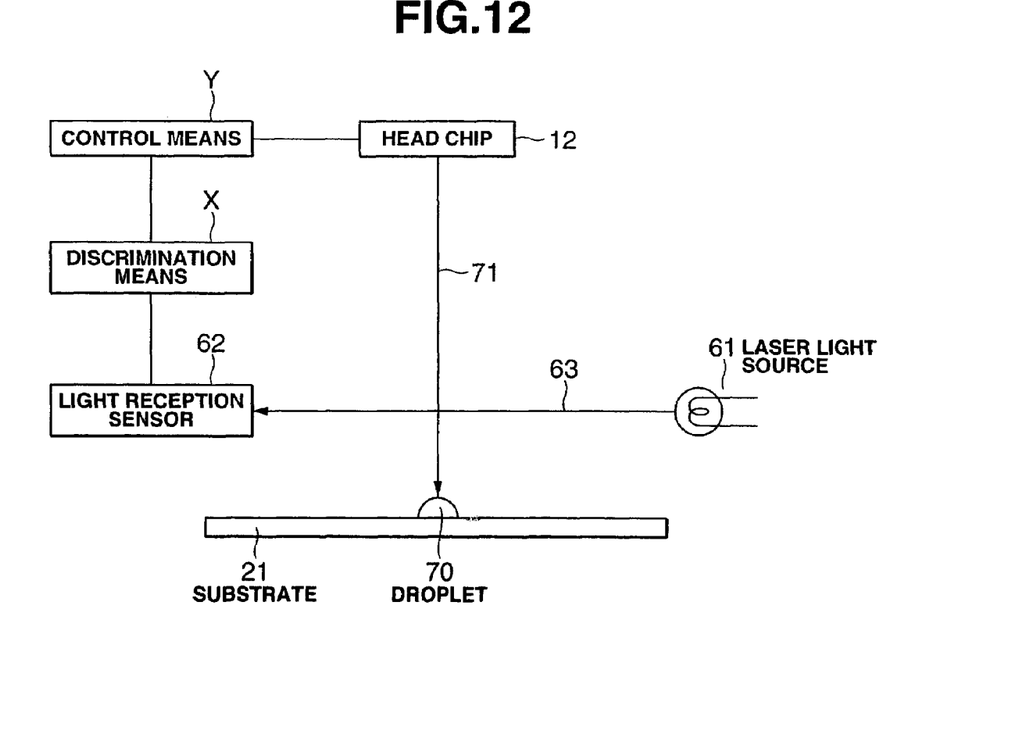
FIG. 12 is an explanatory diagram of means for optically detecting the defective discharge.

In the present embodiment, as a method of discriminating the defective discharge of a nozzle, adopted is a method of optically detecting the droplet discharge. FIG. 12 is a structural diagram for optically detecting the droplet discharge, and illustrated therein are a head chip 12, a spotting substrate 21, a droplet 70 containing protein, a droplet trajectory 71, a laser light source 61, a light reception sensor 62, and a laser beam 63.

For example, in the control means Y structured by including a CPU, when a drive signal is supplied, the droplet 70 is discharged from the head chip 12 toward the substrate 21. If an optical detection means structured from the laser light source 61 and light reception sensor 62 is disposed at the position in which the droplet trajectory 71 and the laser beam 63 intersect, the detection level of the light reception sensor 62 will change when the droplet 70 intersects with the laser beam 63, and the discharge of the droplet 70 may thereby be confirmed. In other words, when the droplet 70 passes through the laser beam 63, the output level of the light reception sensor 62 changes in correspondence with the passing of the droplet. At the discharge timing of the droplet 70, if the detection level of the light reception sensor 62 changes once, it can be discriminated that a single droplet 70 has been discharged (or passed through), and it becomes possible to optically detect the defective discharge of a nozzle. The output change of the light reception sensor 62 is detected, for instance, with the discrimination means X structured from a differentiation circuit and a level comparator. This discrimination result is further sent to the control means Y, and, in the control means Y, generated is a drive control signal for selecting and driving a discharge mechanism (microdispenser 10a) capable of operating normally. This drive control signal is sent to the head chip 12. As described above, in the control means Y, discharge control of the solution containing a biological sample is performed by selecting a discharge mechanism that is not of a defective discharge state in accordance with the result of discriminating a defective discharge with the discrimination means X.

The solution containing protein spotted on the substrate 21 forms a protein chip by being chemically adsorbed on the substrate 21. As a solvent containing protein, it is desirable to employ a solvent in which the spotting shape becomes an approximate circle upon being adhered on the substrate 21, and which does not cause cross contamination among the adjacent discharged spots as a result of the discharged spots expanding. As such a solvent, there is no particular limitation so as long as it does not degenerate the protein and offers stable discharge characteristics. In order to enable a stable droplet discharge, it is desirable that the viscosity be within a range of 1 mNs/m$^2$ to 20 mNs/m$^2$, and surface tension of 30 mN/m to 50 mN/m.

Nevertheless, in the foregoing method, since it is difficult to accurately foresee the trajectory 71 in advance, even when the droplet 70 is discharged from the head chip 12, a defective discharge cannot be discriminated unless the laser light source 61 and light reception sensor 62 are disposed at a position in which the trajectory 71 and laser beam 63 intersect. In anticipation of such a case, it is preferable to employ a scheme where the trajectory 71 and laser beam 63 will intersect as much as possible by reciprocating the two in intersecting directions on paper while retaining the relative positional relationship of the laser light source 61 and light reception sensor 62.

As a means for optically detecting the discharge of the droplet 70, in addition to the foregoing example, for instance, a droplet may be test shot on a dummy area 22, and the existence of a discharge of the droplet 70 may be detected with the CCD sensor 50 (c.f. FIG. 1). After the existence of a defective discharge has been optically judged as described above, a nozzle having a favorable discharge status is selected to prepare a protein chip.

Incidentally, in the foregoing description, although an example of preparing a protein chip was explained, the present invention is not limited thereto, and may be applied to the dispensing of biological samples for preparing any and all microchips. For example, a DNA microarray can be prepared by discharging a single strand DNA from the head chip onto the substrate and forming spots in an array shape. In order to prepare a DNA microarray, for instance, while introducing a thiol group to the DNA strand terminal on the one hand, by introducing a maleimide group on the surface of the substrate 21, it is possible to stably fix a probe DNA via the bonding of the two groups.

Moreover, in the foregoing case, as the single strand DNA to become the probe DNA, employed may be those having a base sequence complementary to the target DNA, for example, a single strand DNA obtained by splicing with a restricted enzyme the DNA strand extracted from the biological material and refined through segregation with electrophoresis, or chemically synthesized oligonucleotide, PCR (polymerase chain reaction) product, cDNA or the like. Meanwhile, as the DNA target, employed may be those in which the DNA strand extracted from the biological sample has been split with a gene splitting enzyme or supersonic treatment, or a single strand DNA or the like which has been amplified with PCR from a specific DNA strand. Further, in addition to DNA, nucleic acid-like substances such as PNA or CNA, and RNA or the like may also be employed as the probe or target.

Moreover, as the means for discriminating the defective discharge of a solution upon employing an optical detection means, in addition to the electrostatic system described above as the discharge means of a solution containing a biological sample, also employed may be a piezo jet system which converts the electric energy, which is applied to an electromechanical conversion element such as a piezo element, into mechanical energy, adjusts the internal pressure of the solvent filled inside the pressurized chamber with the displacement of the diaphragm, and discharges a droplet from a nozzle hole via an orifice. Further, also employed may be a bubble jet system which converts the electric energy applied to a heat generation resistor into thermal energy, and discharges a droplet from a nozzle hole via an orifice by generating air bubbles in the solvent. In consideration of the influence on the biological sample, it is preferable to employ the electrostatic system or piezo jet system which do not accompany instantaneous heat generation. In addition, the present invention is not only applicable to the manufacture of probe arrays, but may also be applied in the manufacture of desired inspection kits or the like in which a plurality of different reagents is discharged from the respective nozzles onto the solid phase surface.

What is claimed is:

1. A dispensing device, comprising:
   an electrode substrate having a plurality of separate electrodes formed in correspondence with each of a plurality of pressurized chambers to be filled with a solution containing a biological sample;
   a pressurized chamber substrate disposed so as to face said electrode substrate in a minute gap, having a discharge mechanism for adjusting the pressure inside said pressurized chamber by mechanical displacement of an elastically deforming diaphragm with an electrostatic force corresponding to a potential difference with said separate electrodes, and discharging said solution from a nozzle hole;
   a drive voltage generation circuit, connected between said diaphragm and said separate electrodes, for applying a drive voltage of a prescribed waveform between said diaphragm and said separate electrodes in order to discharge said solution from said nozzle hole;
   a current detection circuit, which is connected between said diaphragm and said separate electrodes, configured to detect a current flowing between said diaphragm and separate electrodes during the period from the rising edge of the pulse of said drive voltage to the termination of discharge of the solution; and
   discrimination means for comparing the detected current with a pre-stored normal current and for discriminating the existence of a defective discharge of the solution as a result of whether a peak waveform of a differential waveform of the current detected during the period with the current detection circuit appears on the positive side two consecutive times.

2. A dispensing device as in claim 1, wherein said current detection circuit detects said current during the period in which said diaphragm elastically deforms toward said separate electrodes or during the period in which said diaphragm elastically deforms away from said separate electrodes.

3. A dispensing device as in claim 1, wherein said discrimination means performs said discrimination by comparing said detected current with a pre-stored current to be employed upon a normal drive.

4. The dispensing device according to claim 2, wherein said discrimination means performs said discrimination by comparing said detected current with a pre-stored current to be employed upon a normal drive.

5. A dispensing device as in claim 1, further comprising recovery means for recovering the discharge mechanism which resulted in a defective discharge to a normal state.

6. The dispensing device according to claim 5, wherein said recovery means is suction means of a solution containing a biological sample.

7. A dispensing device as in of claim 1, wherein said biological sample is protein.

8. A dispensing device as in claim 2, wherein said biological sample is nucleic acid.

9. A method of detecting a defective discharge of a solution containing a biological sample in a discharge mechanism for adjusting the pressure inside said pressurized chamber by mechanical displacement of an elastically deforming diaphragm, which is disposed so as to face an electrode substrate in a minute gap having a plurality of separate electrodes formed in correspondence with each of the plurality of pressurized chambers to be filled with a solution containing a biological sample, with the electrostatic force corresponding to the potential difference with said separate electrodes, and discharging said solution from a nozzle hole, comprising the steps of:
   applying, under the control of a drive voltage generator circuit connected between said diaphragm and said separate electrodes, a drive voltage of a prescribed waveform between said diaphragm and said separate electrodes in order to discharge said solution from said nozzle hole;
   detecting, under the control of a current detection circuit connected, separately from said drive voltage generation circuit, between said diaphragm and said separate electrodes, a current flowing between said diaphragm and separate electrodes during the period from the rising edge of the pulse of said drive voltage to the termination of discharge of the solution when said drive voltage is applied; and
   discriminating the existence of a defective discharge of the solution based on whether a peak waveform of a differential waveform of the current detected during the period appears on the positive side two consecutive times.

10. A dispensing method, comprising the steps of:
    discriminating a defective discharge of a discharge mechanism with a method according to claim 9 as a preparatory step for spotting a solution containing a biological sample on a substrate; and
    selecting a discharge mechanism in which the discharge status is not defective and spotting said solution on the substrate.

11. The dispensing method according to claim 10, further comprising a step of preparing a microarray by spotting said solution containing a biological sample on an array.

12. The dispensing method according to claim 10, further comprising a step of preparing a protein chip by spotting said solution containing a biological sample on an array.

* * * * *